United States Patent [19]

Cooper

[11] 4,388,476

[45] Jun. 14, 1983

[54] HYDROFORMYLATION PROCESS WITH RHODIUM CATALYST AND OXYGEN STABILIZATION THEREOF

[75] Inventor: James L. Cooper, Longview, Tex.

[73] Assignee: Eastman Kodak Company, Rochester, N.Y.

[21] Appl. No.: 259,399

[22] Filed: May 1, 1981

[51] Int. Cl.$^3$ ............................................. C07C 45/50
[52] U.S. Cl. .................................. 568/451; 568/452; 568/909
[58] Field of Search ............... 568/451, 452, 453, 454, 568/456, 882, 909, 883

[56] References Cited

U.S. PATENT DOCUMENTS

| | | | |
|---|---|---|---|
| 2,880,241 | 3/1959 | Hughes | 568/909 |
| 3,463,741 | 8/1969 | Russell | 568/451 |
| 3,520,937 | 7/1970 | Moell et al. | 568/456 |
| 3,527,809 | 9/1970 | Pruett et al. | 568/451 |
| 3,579,575 | 5/1971 | Bouniot | 568/451 |
| 3,755,393 | 8/1973 | Kniese et al. | 568/451 |
| 3,920,754 | 11/1975 | Wu et al. | 568/451 |
| 3,932,523 | 1/1976 | Strohmeyer | 568/451 |
| 4,113,754 | 9/1978 | Kummer et al. | 568/451 |
| 4,205,013 | 5/1980 | Weber et al. | 568/451 |
| 4,221,743 | 9/1980 | Halstead | 568/451 |
| 4,225,458 | 9/1980 | Haung | 568/451 |

*Primary Examiner*—Werren B. Lone
*Attorney, Agent, or Firm*—Donald W. Spurrell; Daniel B. Reece, III

[57] ABSTRACT

This invention concerns an oxo process employing unmodified rhodium catalyst for the preparation of aldehydes, principally for the preparation of relatively high proportions of branched isomer, from olefins and synthesis gas. More particularly the invention concerns such a process wherein at least a portion of the reaction medium, e.g., the oxo reactor effluent, is contacted with an oxygen containing gas prior to product recovery by distillation, such that the rhodium is converted to a stable form and not lost by plating out on the distillation column or base heater during the distillation.

15 Claims, No Drawings

HYDROFORMYLATION PROCESS WITH RHODIUM CATALYST AND OXYGEN STABILIZATION THEREOF

This invention is concerned with a process which may be used in either batch or continuous operation, and in pressure autoclave, liquid-overflow, or other oxo apparatus, for the hydroformylation of olefins in the presence of unmodified rhodium oxo catalyst fed initially or recycled to the reaction zone in a form which can readily form an active catalyst species. More specifically, this invention is concerned with stabilizing the rhodium against plating out during distillation of the reactor effluent by contacting the same with an oxygen containing gas prior to distillation.

The term "modified" as used herein means that the rhodium is associated with such ligands as the well known alkyl or aryl phosphines, phosphites, arsines, and stibines disclosed, e.g., in U.S. Pat. No. 3,527,809. The term "unmodified" means that the rhodium is present as any of the various complexes with carbon monoxide (hydrogen may also be present in the complex) which form active catalyst species in the reaction zone. Such complexes are described for example, in U.S. Pat. No. 2,880,241.

One of the important objects of this invention is to optimize production of valuable branched chain aldehyde products relative to that obtained from prior catalysts such as phosphine modified cobalt. For example, in regard to butyraldehyde oxo products, the lowest ratio of normal to iso obtainable with commercial cobalt catalysts is on the order of 1.6 to 1.8. A lower ratio is desirable, however, since isobutyraldehyde is a valuable precursor for such materials as isobutyric acid, neopentyl glycol which is a component of coatings and 2,2,4-trimethyl-1,3-pentanediol monoisobutyrate which is a coalescing aid for paints. Another important branched aldehyde is isovaleraldehyde, a precursor to isovaleric acid which has great value as a nutrient additive for cattle feed. The present process yields high proportions of branched aldehyde products, and in the case of butyraldehyde, the ratio of normal to iso ranges from 0.9 to 1.5.

In the case of the unmodified rhodium and to a lesser extent with modified rhodium, distillation of the reactor effluent causes a large portion of the rhodium metal to plate out in the distillation column and/or base heater in a form which is not regenerable in any practical sense. This rhodium loss has rendered rhodium catalyzed processes uneconomical and as a consequence processes have not heretofore been developed to give the high proportions of branched aldehyde products attained by the present invention.

In the present process, treatment of the reactor effluent prior to distillation with an oxygen containing gas forms a rhodium compound, e.g., rhodium butyrate, that does not plate out during the effluent distillation. This oxygen treatment also restores the oxo activity of the rhodium catalyst, and converts it to a soluble form, such as the organic carboxylate, which can rapidly form active catalyst species upon reintroduction to the reaction zone. It is important to this invention that the effluent distillation temperature be maintained below about 120° C., preferably below about 110° C., to insure that essentially complete catalytic activity is restored by the air treatment.

The invention is broadly defined therefore, as a process for preparing aldehyde product from one or more olefins comprising contacting in a reactor at least one olefin with carbon monoxide and hydrogen in the presence of a rhodium catalyst to produce said product, contacting reactor effluent with an oxygen containing gas to convert the rhodium to a carboxylate, and distilling the oxygen treated effluent below about 120° C.

In accordance with more specific parameters, the unbranched to branched-chain aldehydes produced are in the ratio of about 1.2 or less, the olefins are preferably alpha having up to 20 carbon atoms, the hydroformylation temperatures are from about 20° C. to about 300° C., preferably from about 120° C. to about 180° C., and the pressures are from about 15 to about 10,000 psig, with from about 1,000 to about 5,000 psig being preferred, and from about 1,500 to about 3,000 psig being most preferred.

In carrying out the present process in a continuous manner, conventional, continuous oxo equipment well known to those skilled in the art may be used such as an overflow reactor from which the catalyst leaves with the aldehyde product, high pressure chiller, vapor-liquid separator, pressure let-down valve, (optional-low boiler removal column for olefins, etc.), air treatment unit, product recovery distillation column, (optional-base overflow chiller), and catalyst recirculation means.

In operation, the syn gas is introduced into the reactor in a continuous manner by means, for example, of a primary compressor with the ratio of hydrogen to carbon monoxide selected according to the particular olefin being hydroformylated and the reaction conditions present, as is well known in the art. Generally, the molar ratio of hydrogen to carbon monoxide in the reactor will be in the range of from about 0.5 to about 10, with from about 1 to about 2 being preferred. The syn gas preferably is present in a molar excess (total moles of $H_2+CO$) with respect to the olefin and the molar ratio varies typically from about 1 to about 10, preferably from above about 1 to about 2.

The olefin is fed to the reactor by means of suitable pumps capable of operating under substantial pressures and the feed rates of the olefin and syn gas are selected to maintain the above recited molar ratios of these reactants in the reactor. Typical useful olefins include $\alpha$-olefins containing from 2 to 20 carbon atoms and preferably from 2 to 10 carbon atoms, straight-chain or branched-chain, and optionally containing groups or substituents which do not interfere with the hydroformylation process. Illustrative such $\alpha$-olefins are ethylene, propylene, 1-butene, 2-methyl-1-butene, 1-pentene, 1-hexene, 1-heptene, 1-octene, 2-ethyl-1-hexene, 1-dodecene and 1-octadecene. Also applicable to the present process are the internal olefins such as butene-2 and cyclic olefins such as cyclooctene.

If desired, mixtures of olefins can be fed to the reaction zone such as a mixture of propylene, isobutylene and butene-1. Such mixtures hydroformylate at production rates and normal to isobutyraldehyde ratios essentially equivalent to that achieved with propylene alone.

The recycled rhodium may be introduced as the carboxylate into the reactor zone along with the solvent through suitable liquid pressure pumping means and interacts with the syn gas to form a complex, active catalyst species.

Any suitable solvent which does not adversely affect the process and which is inert with respect to the catalyst, olefin feed, synthesis gas and the hydroformylation products may be used. Inert solvents of this nature are well known to the art and include xylene and their substituted derivatives, pentanes, naphtha, kerosene, mineral oils, cyclohexane, cyclopentane, ethers, esters, etheresters, alcohols, acetals, ketones and preferably benzene, toluene, ethano, isopropanol, ethylene glycol monomethylether and ethylene glycol dimethylether, and most preferably 2,2,4-trimethyl-1,3-pentanediol monoisobutyrate (TMPDMI), and its isomers, and the by-products such as alcohols, esters, acetals, and hydroxyaldehydes produced in the hydroformylation reaction and retained as high boiling liquids at the bottom of the distillation column. The solvent system, preferably a high boiler, is introduced into the reactor along with the catalyst and allowed to recycle therewith after the distillation and catalyst regeneration steps. It is particularly noted that when the reactor effluent contains TMPDMI as a solvent, oxidation of the aldehyde product to acid is markedly retarded. From the standpoint therefore, of increased aldehyde yield and purity, this phenomenon is an unexpected adjunct of the present invention.

The present process can be carried out with very small amounts of catalyst such as that containing about $1 \times 10^{-8}$ moles of rhodium (metal) per mole of olefin feed. However, such low catalyst concentrations are not commercially desirable since the reaction rates are low. The upper catalyst concentration is essentially unlimited and appears to be dictated principally by the high cost of rhodium and the fact that no advantage is evident in the use of catalyst containing above about $1 \times 10^{-1}$ moles of rhodium per mole of olefin. A concentration of rhodium of from about $1 \times 10^{-6}$ moles to about $5 \times 10^{-2}$ moles per mole of olefin is preferred, and from about $1 \times 10^{-4}$ to about $1 \times 10^{-2}$ is most preferred.

The air treatment step may be carried out at atmospheric conditions in simple equipment, such as a tank with continuous feed and continuous removal of catalyst. A wide range of temperatures may be used for the air treatment such as from 25° C. to 80° C. with a preferred range being from 50° C. to 60° C. The reaction time required for efficient oxidation of the rhodium catalyst at 25° C. to 80° C. can take up to 12 hours or longer. Within the scope of this invention the preferred oxidation conditions are from 20 minutes to 40 minutes at 50° C. to 60° C. The number of moles of oxygen per mole of rhodium for the oxidation step is not critical, but it is preferred to employ at least a 1/1-$O_2$/Rh molar ratio in excess of other oxygen scavengers which may be present.

The following examples further illustrate the present invention but should not be construed as limiting the same in any manner.

EXAMPLE 1

Preparation of Rhodium Isobutyrate

An aqueous solution of sodium isobutyrate is prepared by dissolving 4 grams of sodium hydroxide and 9 grams of isobutyric acid in 100 milliliters of water at room temperature. Hydrated rhodium trichloride (2.5 grams) is added to the aqueous solution and stirred at room temperature until complete solution occurs. The bright red solution is heated with stirring on at 100° C. for 1 hour, during which time a yellow green precipitate of rhodium isobutyrate forms. The mixture is cooled and the precipitate removed by filtration on a fine glass frit. The precipitate is washed thoroughly with water and dried under a stream of dry nitrogen. The precipitate is then dissolved in about 60 milliliters of pure isobutyric acid and filtered through a fine glass frit to remove traces of insoluble material. A suitable volume of this solution is made up with more isobutyric acid to give a known rhodium metal concentration.

EXAMPLE 2

A batch of oxo effluent for the use in distillations below was prepared as follows:

Rhodium isobutyrate solution (10 ml, 0.1 mg Rh) was combined with 92 ml (83.2 grams) of 2,2,4-trimethyl-1,3-pentanediol monoisobutyrate (TMPDMI) in a 300 ml stainless steel autoclave equipped with a stirrer and automatic cooling. After chilling the autoclave in dry ice, propylene (40 grams) was charged thereinto. Synthesis gas was then pressured in at 2,000 psig and the temperature raised to 150° C., the pressure increasing to 2,500 psig. This pressure was maintained throughout the 30-minute run time. The system was cooled and vented. The weight gain and production rate of the butyraldehyde were determined. The effluent comprising catalyst solution and butyraldehye product was then pumped out of the vent tank into a polypropylene container which was stored under nitrogen at 5° C. until needed. For the experiment of Example 5 below, the effluent was air oxidized for 30 minutes at 55° C. to convert the catalyst to rhodium butyrate or isobutyrate.

EXAMPLE 3

This example gives the general distillation procedure for both the air treated and straight effluent from Example 2, care being taken not to allow air to come into contact with the straight effluent. For the distillations, the effluent is transferred into a stainless steel distillation column to a suitable level and the distillation initiated by starting the base heater set at 120° C., reboiler circulation pump, and the base taken off pump set at 600 ml/hr in concert with a column feed pump which pumps reactor effluent into the column at a rate to hold the desired column level. Butyraldehyde is distilled overhead and catalyst base product pumped into a lower base product tank while bringing the column to equilibrium, after which an adequate amount of the steady state base product (SSBP) is collected in an upper tank, and the column then shut down. Each column feed (CF) of effluent was analyzed by gas-liquid chromatography and the percent TMPDMI by weight determined. Gas-liquid chromatographic and atomic absorption spectroscopic analysis have shown that no rhodium or TMPDMI is distilled overhead.

EXAMPLE 4

For the evaluation of the catalytic activity of the air treated and straight CF and their corresponding SSBP, the autoclave reaction of Example 2 was used. Each CF and its corresponding SSBP were weighed out to contain the same amount of TMPDMI by analysis which, theoretically, should contain the same amount of rhodium if none were lost in the distillation. The weight gains and production rates of each CF and SSBP were then compared. The results are given in the following table which shows that the SSBP of the air treated CF had a slightly increased catalytic activity over the CF (Example 5), while the SSBP of the non-air treated CF had only about 50% the activity of the CF (Example 6).

| Butyraldehyde Distillations | | |
|---|---|---|
| | Production Rate, lb/ft³-hr | |
| Example No. | CF | SSBP |
| 5 | 44.7 | 47.5 |
| 6 | 50.7 | 25.5 |

The invention has been described in detail with particular reference to preferred embodiments thereof, but it will be understood that variations and modifications can be effected within the spirit and scope of the invention.

We claim:

1. A hydroformylation process comprising contacting at least one alpha or internal olefin of from 2 to 20 carbon atoms in a reaction zone at a temperature of from about 20° C. to about 300° C. and a pressure of from about 15 psig to about 10,000 psig with hydrogen, carbon monoxide and a catayst consisting essentially of unmodified rhodium for a sufficient period of time to produce aldehyde product, treating reactor effluent with an oxygen containing gas, and separating said product from said effluent in a distillation zone at a temperature of about 120° C. or less to leave a base product containing a rhodium salt of a carboxylic acid.

2. The hydroformylation process according to claim 1 wherein said base product is returned to said reaction zone.

3. The hydroformylation process according to claim 1 wherein said reaction zone is operated at a temperature of between about 60° C. and 200° C.

4. The hydroformylation process according to claim 1 wherein said reaction zone is operated at a temperature of from about 125° C. to 175° C., and a pressure of between about 2,000 psig and 2,500 psig.

5. The hydroformylation process according to claim 1 wherein the molar ratio of said hydrogen to carbon monoxide is at least 0.5.

6. The hydroformylation process according to claim 5 wherein the total moles of hydrogen and carbon monoxide are present in said reaction zone in the ratio range of from 1 to about 10 with respect to moles of said olefin.

7. The hydroformylation process according to claim 1 wherein said alpha olefin is selected from one or more of ethylene, propylene, 1-butene, isobutylene, 2-methyl-1-butene, 1-pentene, 1-hexene, 1-heptene and 1-octene.

8. The hydroformylation process according to claim 1 wherein a solvent is selected from benzene, toluene, ethanol, isopropanol, ethylene glycol monomethyl-ether, ethylene glycol dimethylether, and 2,2,4-trimethyl-1,3-pentanediol monoisobutyrate.

9. The hydroformylation process according to claim 8 wherein the solvent is 2,2,4-trimethyl-1,3-pentanediol monoisobutyrate.

10. The hydroformylation process according to claim 7 wherein said unmodified rhodium catalyst is present in said reaction zone in an amount of between about $1 \times 10^{-8}$ to about $1 \times 10^{-1}$ mol. of rhodium metal per mole of said alpha olefin.

11. The hydroformylation process according to claim 1 wherein said distillation zone is operated at a temperature of less than 110° C.

12. The hydroformylation process according to claim 1 wherein said oxygen containing gas is air.

13. The hydroformylation process according to claim 1 wherein the molar ratio of oxygen to rhodium is at least 1.

14. The hydroformylation process according to claim 1 wherein the oxygen treatment is carried out at temperatures from about 25° C. to about 80° C.

15. The process of claim 14 wherein the treatment temperatures are from about 50° C. to about 60° C.

* * * * *